United States Patent
Fagan et al.

(10) Patent No.: US 6,206,915 B1
(45) Date of Patent: Mar. 27, 2001

(54) DRUG STORING AND METERING STENT

(75) Inventors: John R. Fagan, Pepperell, MA (US); Chirag B. Shah, Nashua, NH (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

(21) Appl. No.: 09/162,540

(22) Filed: Sep. 29, 1998

(51) Int. Cl.[7] .................................................. A61F 2/04
(52) U.S. Cl. ..................... 623/1.42; 623/1.44; 623/1.15; 623/23.7
(58) Field of Search .................... 623/1, 12, 1.27, 623/1.15, 1.42, 1.44–1.48

(56) References Cited

U.S. PATENT DOCUMENTS

| | | | |
|---|---|---|---|
| 4,417,576 | 11/1983 | Baran | 128/207.15 |
| 5,707,385 | 1/1998 | Williams | 606/192 |
| 5,733,326 * | 3/1998 | Tomonto et al. | 623/1 |
| 5,735,897 * | 4/1998 | Buirge | 623/12 |
| 5,788,626 * | 8/1998 | Thompson | 600/36 |
| 5,824,050 * | 10/1998 | Karwoski et al. | 623/1 |
| 5,843,166 * | 12/1998 | Lentz et al. | 623/1 |
| 5,858,556 * | 1/1999 | Eckert et al. | 428/586 |
| 5,948,018 * | 9/1999 | Dereume et al. | 623/1 |

* cited by examiner

Primary Examiner—David H. Willse
Assistant Examiner—Suzette J. Jackson
(74) Attorney, Agent, or Firm—Sterne, Kessler, Goldstein & Fox P.L.L.C.

(57) ABSTRACT

A drug storing and metering stent for placement within a vessel comprising an outer member having a lumen, an inner member positioned within the lumen of the outer member. A space separates the inner member from the outer member and within which space a therapeutic drug is disposed. The stent includes at least one protrusion provided on at least one of the inner and outer members and extending across the space so as to cause a friction fit between the inner and outer members. The stent also includes a pattern of perforation across both the inner and outer members to permit the stent to expand radially. The invention also relates to a method of making such a stent, and a method of releasing a therapeutic drug within a vessel.

18 Claims, 2 Drawing Sheets

DRUG STORING AND METERING STENT

TECHNICAL FIELD

This present invention relates to stents for placement within a vessel, such as a coronary artery, and more particularly, to stents designed for storing and releasing therapeutic drugs, such as those used in the treatment of restenosis.

BACKGROUND ART

Disease, injury and/or surgery can result in localized tissue damage within a vessel and possibly occlusion within the vessel. Angioplasty is a procedure which may be used to lessen the amount of occlusion, whereby a balloon is inserted into an occluded vessel and subsequently inflated to dilate the occluded area. In some instances, the balloon may damage the vessel wall during inflation. As a result, in about 30 to 50% of the cases, the initial increase in the vessel dimensions may be followed by a localized re-narrowing (i.e., restenosis) of the vessel at the occluded area over a period of about three to six months. Restenosis may be the results of hyperplasia within the neointima, vascular remodeling within the vessel, or shrinkage in the overall vessel dimensions. To prevent re-narrowing of the vessel, expandable stents, for example, have been implanted at the site of occlusion (i.e., constriction site), so that the a pathway may be maintain for fluid to flow therethrough.

There are a variety of methods currently used to implant an expandable stent within a vessel. A commonly used method first mounts an expandable stent in a non-expanded state on a balloon portion of a catheter. Subsequently, the catheter is maneuvered, with the stent thereon, along the vessel to the constriction site. Once the stent is at the constriction site, the balloon is dilated to expand the stent, and thus enlarging the vessel at the site of constriction. However, as with angioplasty, restenosis may subsequently result at the constriction site, despite the presence of the stent thereat. In particular, tissue growth may occur across the pattern of perforation (such a pattern is typically necessary to permit expansion of the stent from a non-expanded state) on the stent and into the stent lumen.

To reduce or prevent the occurrence of restenosis, there are stent designs which incorporate a therapeutic drug into or onto the stent body, which drug may diffuse or be released after the placement of the stent into a vessel. In one design, the therapeutic drug is coated onto the surface of the stent body. As fluid flows across the surface of the stent, the coat degrades and releases the therapeutic drug from the stent. However, such a design may permit the drug to be released too quickly. Consequently, the desired reduction in the occurrence of restenosis may not result. In another design, the therapeutic drug is incorporated into a strip of biodegradable material, and the strip placed onto the body of, for instance, a non-degradable stent. In this design, as the strip biodegrades the therapeutic drug is released at a rate at which the strip biodegrades. However, the use of a biodegradable strip may not provide a sufficient amount of a therapeutic drug necessary to reduce or prevent the occurrence of restenosis. With other designs, the therapeutic drug may be incorporated throughout the body or within different biodegradable layers of a biodegradable stent, so that the drug can be released as the stent biodegrades. The incorporation of the therapeutic drug into the body of the biodegradable stent may increase the total amount of drug over that used in the strip embodiment. However, the drug concentration must be so balanced so as not to affect the polymeric make-up of the stent, and thus the ability of the stent to biodegrade over a sufficiently long period during which restenosis may occur. At such a concentration, the amount of therapeutic drug may not be sufficient to reduce or prevent restenosis over the period necessary.

Accordingly, it is desirable to provide an expandable stent which can store a sufficient amount of therapeutic drug, which can vary the concentration of the drug without compromising the characteristics of the stent, and which can release the drug over a sufficiently long amount of time in a sufficient concentration to reduce and/or prevent the occurrence of restenosis.

SUMMARY OF THE INVENTION

The present invention is directed to a drug storing and metering stent designed for placement within a body vessel. In accordance with one embodiment of the invention, the stent, adapted to expand and remain in an enlarged diameter against the vessel wall, includes an outer member having a lumen and a cannulated inner member positioned within the lumen of the outer member. The stent further includes a space separating the inner member from the outer member and being situated between an outer surface of the inner member and the inner surface of the outer member. At least one protrusion is provided on at least one of the inner and outer members, and which protrusion extends across the space so as to create a friction fit between the inner and the outer members. As the stent is designed to deliver a therapeutic drug to a local site, for example, a constriction site caused by restenosis, a therapeutic drug may be disposed within the space between the inner and outer members. To maintain the drug within the space, the drug may be imbedded within a carrier, such as a bioabsorbable gel. The stent further includes a pattern of perforation extending from the outer member, across the space, and through the inner member. The presence of the perforation permits the stent to expand radially in diameter.

The stent may be manufactured, in accordance with one embodiment of the present invention, by positioning an inner tubular member having a predetermined outer diameter within an outer tubular member having a larger inner diameter so that they are substantially concentrically aligned. The difference between the diameters of the members defines a space between the first and second members. Once the members have been aligned at least one protrusion is caused to extend across the space from one of the inner and outer members. The protrusion must extend sufficiently across the space, so as to provide a friction fit between the inner and outer members. It should be appreciated that the protrusion or protrusions may be provided on the outer member, the inner member, or both, and may be provided on one or both members prior to the positioning of the inner member within the outer member. A therapeutic drug may next be disposed in the space between the outer and inner members. Thereafter, a pattern of perforation may be etched, for example, by laser, through the inner and outer members to provide the stent with the ability to expand. Alternatively, the perforation may be etched in the stent prior to the placement of the therapeutic drug within the space.

The stent, manufactured in accordance with an embodiment of the invention, may be placed within a vessel, for instance, a coronary artery, in a non-expanded state. Once it has been maneuvered to a site of interest, the stent may be expanded by a balloon catheter, so that with its expanded diameter, the stent is securely positioned within the vessel. The stent and the space between the outer and inner members may then be exposed to fluid flow within the vessel, so as to cause the therapeutic drug to be diffused or released into the vessel.

DETAILED DESCRIPTION OF SPECIFIC EMBODIMENTS

Figure 1:
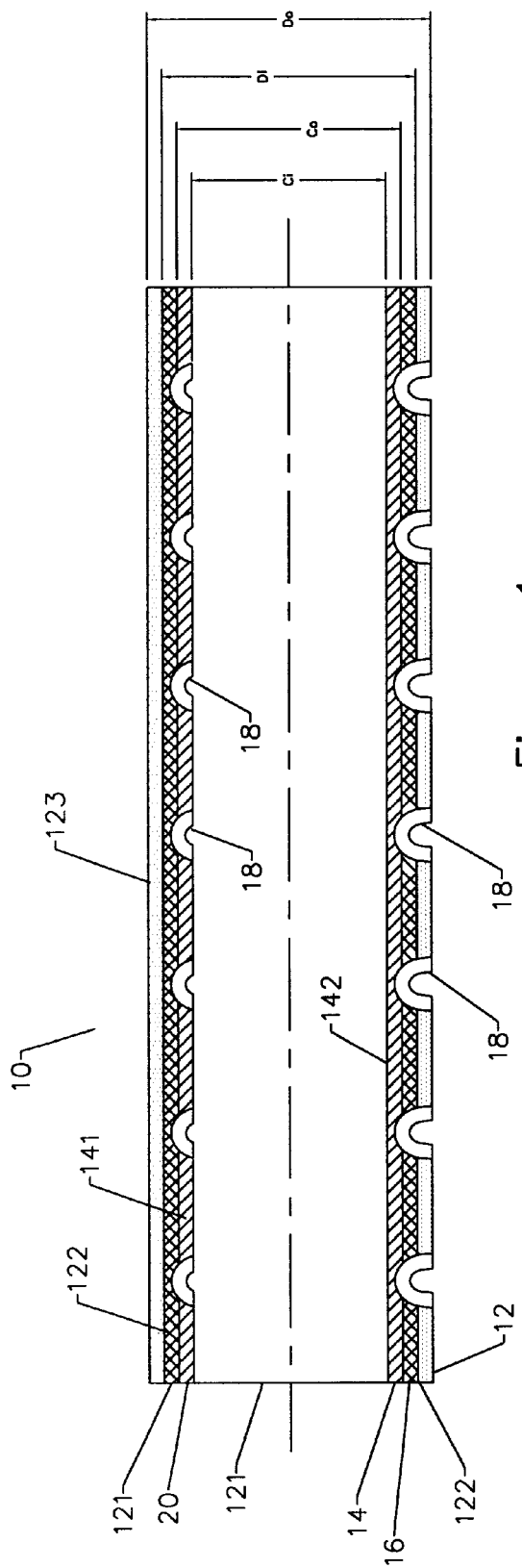
FIG. 1 is a longitudinal sectional view of a stent in accordance with an embodiment of the present invention.
Figure 2:
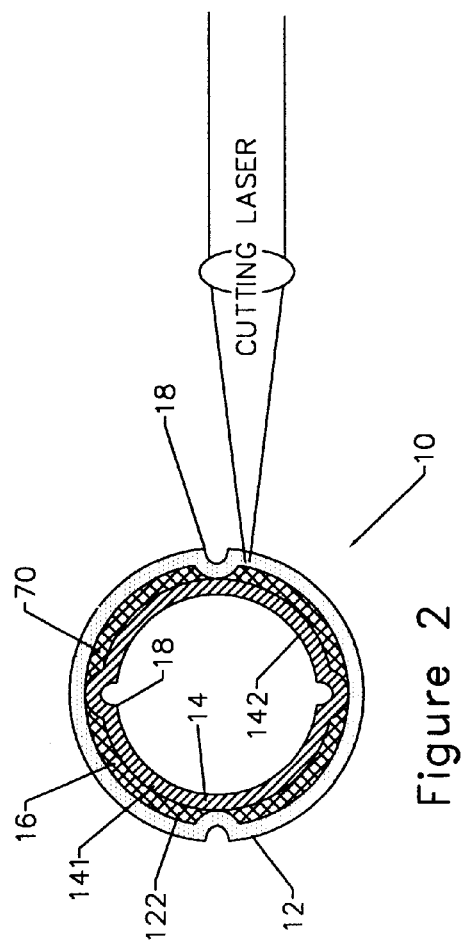
FIG. 2 illustrates an end view of the stent shown in FIG. 1.

Referring now to the drawings, FIGS. 1 and 2 illustrate a stent 10 in accordance with one embodiment of the present invention. The stent 10, designed for storing drug and subsequently releasing the drug in vivo, includes an outer member 12, having a lumen 121, and a cannulated inner member 14 disposed within the lumen 121 of the outer member 12. As shown in FIG. 1, the outer member 12, being substantially cylindrical in shape, includes an outer diameter $D_o$, an inner diameter $D_i$, and an inner surface 122 defined by the lumen 121. The inner member 14, also substantially cylindrical in shape, includes an outer diameter $C_o$, an inner diameter $C_i$, and an outer surface 141. It should be appreciated that although the inner member 14 and outer member 12 are shown to be substantially cylindrical in shape, the inner and outer members may be, for instance, hexagonal or octagonal in shape, or may have other suitable shapes, so long as the inner member 14 may be disposed within the lumen 121 of the outer member 12, and the stent 10 subsequently be disposed within a vessel without causing damage to the vessel.

The stent 10 further includes a space 16 separating the inner member 14 from the outer member 12. The space 16, in one embodiment, is defined by a difference between the inner diameter $D_i$ of the outer member 12 and the outer diameter $C_o$ of the inner member 14, and runs substantially circumferentially between the entire outer surface 141 of the inner member 14 and inner surface 122 of the outer member 12. The space 16 may be used to store a therapeutic drug formulated to reduce or prevent, for example, the occurrence of restenosis within a vessel. The drug may be placed and retained within the space 16 by conventional methods known in the art. One conventional method is to embed the drug within a carrier (e.g., bioabsorbable gel, biodegradable polymeric matrix) prior to placing the gel within the space 16.

To permit the inner member 14 to remain within the outer member 12 in the presence of the space 16, the stent 10 is provided with a mechanism to securely position the inner member 14 within the lumen 121 of the outer member 12. In one embodiment, the mechanism includes at least one protrusion 18 or dimple provided on at least one of the inner member 14 and outer member 12. The protrusion 18 preferably extends across the space 16 so as to engage the opposite member, such that a friction fit may be provided between the inner member 14 and the outer member 12. To ensure a secured friction fit between the members, a plurality of protrusions 18 may be provided on the inner member 14 only, on the outer member 12 only, or on both the inner and outer members. The number, as well as the size of the protrusions 18, however, should be sufficient so as to permit the maximum desired amount of the therapeutic drug to be placed within the space 16 without compromising the security of the fit.

The stent 10, in accordance with a preferred embodiment of the invention, may be designed to expand radially in diameter from a non-expanded state, shown in FIGS. 1 and 2. Looking now at FIG. 3, to permit expansion, the stent 10 is provided with a pattern of perforation 30 along its entire length. The pattern of perforation 30 preferably extends from the outer member 12, across the space 16, and through the inner member 14, so that the inner and outer members may have substantially similar patterns of perforation. By providing similar patterns of perforation, both the inner member 14 and outer member 12 may expand proportionately with little or no interference from the other member. Moreover, when the members expand proportionately, the friction fit between the inner member 14 and the outer member 12 may be maintained. Although the friction fit can be maintained, it is preferable that the protrusions 18 be provided with sufficient extension across the space 16 to compensate for any slight unevenness in the radial expansion between the inner member 14 and the outer member 12.

As the stent 10 needs to be placed within a vessel and needs to withstand potential radial compression force from the vessel, the outer and inner members are preferably made from a strong biocompatible material. In one embodiment, the outer and inner members may be made from a rigid metallic material, for example, stainless steel. Other strong biocompatible material may also be used, including, but not limited to, tantalum, nitinol, and MP35N alloy. Furthermore, in a preferred embodiment, the outer member 12 is designed so that it is permitted to contract in a radial direction more than that permitted with the inner member 14. In this manner, a secured friction fit can be ensured between the members in the event there is some radial contraction by the inner member 14. This is important because after the stent 10 has been expanded within the vessel, and the balloon catheter removed (a detailed description of which is provided below), there tends to be some radial contraction of the inner and outer members. If the outer member 12 cannot contract radially more than the inner member 14, the friction fit between the members will lessen or be terminated, thereby compromising the position of the outer member relative to inner member. The inner member 14, as a result, may be moved from within the outer member 12. The outer and inner members of the stent 10 may also be made from a bioabsorbable material if so desired, especially if the need for the stent is only temporary.

The stent 10 of the present invention may be manufactured, according to one embodiment, by first positioning an inner member 14 within an outer member 12, so that they are substantially concentrically aligned. Thereafter, while maintaining the members in substantial concentric alignment, at least one protrusion 18 is caused to extend from one of the inner and outer members, across the space 16, and toward the other member. In particular, if the outer and inner members are to be made from, for instance, a biocompatible metallic material, and if the protrusion 18 is to be provided on the inner member 14, a pointed apparatus may first be placed against an inner surface 142 of the inner member 14. Subsequently, the apparatus may be pushed against the inner surface 142, thereby causing a protrusion 18 to be formed into the space 16 and against the inner surface 122 of the outer member 12. If, on the other hand, the protrusion 18 is to be provided on the outer member 12, the pointed apparatus may initially be placed against an outer surface 123 of the outer member, and subsequently pushed against the outer surface 123 into the space 16, so as to cause a protrusion 18 to be formed against the outer surface 141 of the inner member 14. If additional protrusions 18 on one or both of the members are desired, the processes described may be repeated accordingly. Alternatively, the protrusions 18 may be provided on one or both of the members prior to concentrically aligning the inner member 14 within the outer member 12. When forming the protrusions 18 prior to placing the inner member 14 within the outer member 12, it should be appreciated that the extension of the protrusions 18 should be substantially even, such that the inner member 14 may be substantially concentrically aligned within the outer member 12. In addition, instead of pushing against the inner and/or outer surfaces of the members, the protrusions 18 may also be formed by attaching (e.g., bonding, welding, gluing) a protuberance on the outer surface 141 of the inner member 14 and/or the inner surface 122 outer member 12. The protrusions 18 may also be formed by impression, similar to the formation of knurls by impression.

Once the inner member 14 is securely positioned within the outer member 12, a therapeutic dosage of a drug may next be disposed within the space 16 between the outer and inner members. As indicated previously, the therapeutic drug may be imbedded within a bioabsorbable gel carrier or a biodegradable polymeric matrix to enhance retention of the drug within the space 16. If the amount of therapeutic drug within the space 16 needs to be increased, the size of the space 16 may be increased accordingly by increasing the difference between the inner diameter $D_i$ of the outer member 12 and the outer diameter $C_o$ of the inner member 14. Moreover, since the drug is stored within the space 16, rather than being incorporated within the members making up the stent 10 an increase in the concentration of the drug does not, in any way, compromise the integrity of the stent 10.

Figure 3:
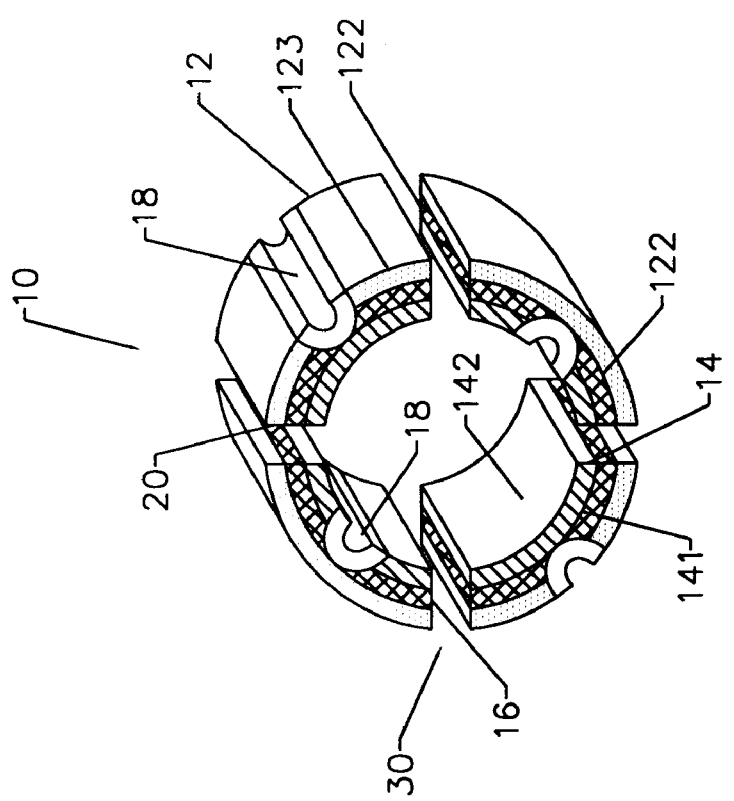
FIG. 3 illustrates a partial view of an end portion of the stent shown in FIG. 2.

After placement of the therapeutic drug within the space 16, the pattern of perforation 30 may be formed on the stent 10, across the outer and inner members. As illustrated in FIG. 3, formation of the pattern of perforation 30 exposes the therapeutic drug within the space 16 along the length of the stent 10. In a preferred embodiment, the pattern of perforation 30 is preferably sufficient so as to permit the stent 10 to expand radially in diameter. The pattern of perforation can be a crossing pattern, an undulating pattern, or any pattern known in the art, which permits radial expansion without substantially compromising the linear or axial displacement of the stent 10. In one method of the invention, the pattern of perforation 30 may be formed by laser etching. Other methods known in the art may also be used, for example, mechanical cutting or chemical etching or electro-discharged machining (EDM). Alternatively, the pattern of perforation 30 may be formed on the stent 10 prior to placement of the therapeutic drug within the space 16 between the inner and outer members.

In another embodiment, the stent 10 of the present invention may be manufactured by initially positioning two substantially flat sheets on one another, with protrusions 18 having been formed on one or both sheets, so as to provide a space 16 between the two sheets. Thereafter, the two sheets may be rolled simultaneously, such that the opposite edges of each sheet may be brought toward one another to form a substantially cylindrical stent 10. The edges may then be secured against one another using methods known in the art, for example, welding or gluing. Once the cylindrical stent 10 is formed, the therapeutic drug may be placed within the space 16. The patterns of perforation may then be formed as described above. It should be appreciated that prior to rolling the sheets into a cylindrical stent 10, the therapeutic drug may, of course, be positioned in the space between the two sheets and/or the patterns of perforation may be provided on the sheets.

Figure 4:
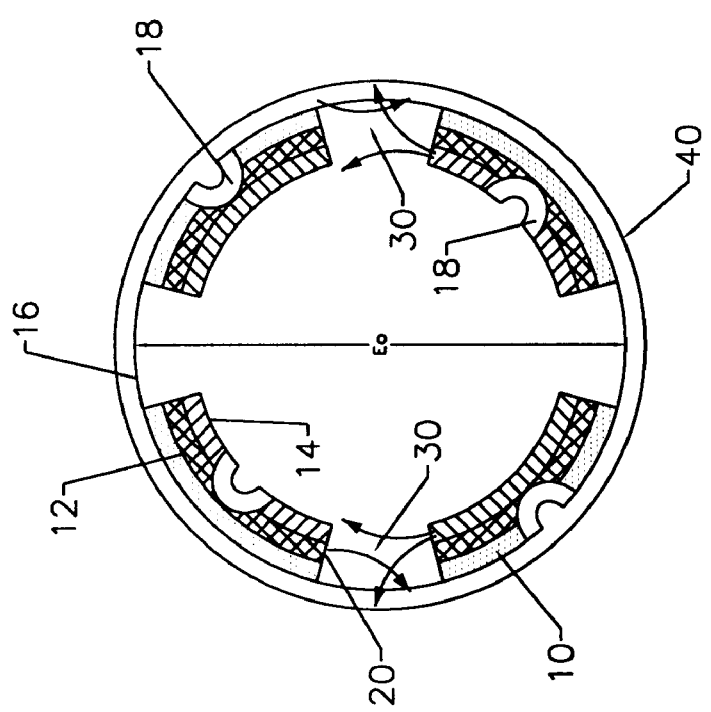
FIG. 4 shows the stent in FIG. 3 in an expanded form.

Looking now at FIG. 4, the stent 10, manufactured in accordance with an embodiment of the present invention, may be placed within a vessel 40, for example, a coronary artery, to release a therapeutic drug stored within the space 16. First, the stent 10 may be placed, in a non-expanded state (FIGS. 1–3), on a balloon portion of a balloon catheter (not shown) by inserting the balloon portion of the catheter into the cannulation of the inner member 14. Next, the catheter is maneuvered, with the stent 10 thereon, along the vessel 40 to a placement site, for instance, a constriction site. Once the stent 10 is at the constriction site, the balloon portion of the catheter is dilated to force the inner member 14 of the stent 10 into an expanded state. As the inner member 14 expands, the protrusions 18 push against the outer member 12 to expand the stent 10, and consequently the constriction site. The stent 10 may continue to expand radially until the outer member 12 is provided with an expanded outer diameter $E_o$, which is preferably substantially similar to the inner diameter of the vessel 40. By providing the outer member 12 with an outer diameter $E_o$, the stent 10 may be securely positioned within the vessel 40. The stent 10, in its expanded state, is sufficiently strong radially, so as to maintain an opening in the flow path of the vessel 40 where the stent 10 is placed. As fluid flows over the surfaces of the stent 10, the therapeutic drug within the space 16, which is now exposed by the pattern of perforation 30, comes into contact with the fluid. The contact of the drug with the fluid flow within the vessel 40 consequently causes the therapeutic drug to be released or diffused from the space 16 and into the vessel 40. Because the amount of therapeutic drug, as well as its concentration, can be stored within the space 16 in a substantial amount (relative to that of a drug which must be incorporated within the stent composition), the release or diffusion of the drug, which may be an anti-restenosis drug, may extend over a sufficiently long period of time locally, in a sufficient concentration to reduce and/or prevent, for example, the occurrence of restenosis.

While the invention has been described in connection with specific embodiments thereof, it will be understood that it is capable of further modification. For example, the drug stored within the space 16, although has been discussed in connection with the reduction of restenosis, may be formulated to have other therapeutic effects, for instance, an anti-proliferative effect. In addition, the stent 10, if so desired, may be designed so that the inner and outer members are not concentrically aligned and/or have fixed outer diameters (i.e., no expansion capability). This application is intended to cover any variations, uses, or adaptations of the invention and including such departures from the present disclosure as come within known or customary practice in the art to which the invention pertains.

We claim:

1. A stent comprising:

an outer member having a lumen;

a cannulated inner member positioned within the lumen of the outer member;

a space separating the inner member from the outer member; and at least one protrusion provided on at least one of the inner and outer members, the protrusion extending across the space, so as to cause a friction fit between the inner and the outer member.

2. A stent as set forth in claim 1 further including a therapeutic drug disposed within the space separating the inner member from the outer member.

3. A stent as set forth in claim 2, wherein the drug is imbedded within a gel.

4. A stent as set forth in claim 1 further including a pattern of perforation extending from the outer member through the inner members, so as to permit the stent to expand in diameter.

5. A stent as set forth in claim 1, wherein the inner and outer member are concentrically aligned.

6. A stent comprising:
    first and second tubular members concentrically aligned about a longitudinal axis, and defining a substantially cylindrical profile;
    a space defined by an outer surface of the second tubular member and an inner surface of the first tubular member, wherein said space contains a therapeutic drug; and
    means for maintaining the space between the second member and the first member, said means also providing a friction fit between the second member and the first member.

7. A stent as set forth in claim 6, wherein means for maintaining includes at least one protrusion extending across the space from at least one of the first and second member.

8. A stent as set forth in claim 6 further including a therapeutic drug disposed within the space between the first and second members.

9. A stent as set forth in claim 6 further including a pattern of perforation extending from the outer member through the inner members, so as to permit the stent to expand in diameter.

10. A method of manufacturing a stent, the method comprising:
    providing a first tubular member having a first initial diameter;
    positioning within the first member, a second tubular member having a second initial diameter, so that a difference between the first and second diameters define a space between the first and second members; and
    causing at least one protrusion to extend across the space from one of the first and second members to maintain the second member within the first member.

11. A method as set forth in claim 10 further including the step of disposing a therapeutic drug in the space between the first and second members.

12. A method as set forth in claim 10 further including the step of etching the pattern of perforation which extends from the outer member through the inner members, so as to permit the members to expand proportionately beyond their respective initial diameters.

13. A method of manufacturing a stent, the method comprising:
    providing a first tubular member having a first initial diameter;
    providing a second tubular member having a second initial diameter, such that when the second member is positioned within the first member a difference between the first and second diameters define a space between the first and second members
    causing at least one protrusion to extend from one of the first and second members toward the other of the first and second members; and
    inserting the second member within the first member, such that the protrusion provides a friction fit between the first and second member.

14. A method as set forth in claim 13 further including the step of disposing a therapeutic drug within the space between the first and second members.

15. A method as set forth in claim 13 further including the step of etching a pattern of perforation which extends from the outer member through the inner members, so as to permit the members to expand proportionately beyond their respective initial diameters.

16. A method of releasing a therapeutic drug within a vessel, the method comprising:
    providing an expandable stent having a second tubular member disposed within a first tubular member, a space separating the second tubular member from the first tubular member, a therapeutic drug disposed within the space, and means for maintaining the space between the second member and the first member, said means also providing a friction fit between the second member and the first member;
    positioning the stent within a vessel;
    expanding the stent radially; and
    permitting fluid within the vessel to contact the drug as the fluid flows through the stent.

17. A method as set forth in claim 16, further comprising:
    exposing the space within which the therapeutic drug is disposed to fluid flow in the vessel, so as to cause the drug to be released into the vessel.

18. A method as set forth in claim 16, wherein the first and second tubular members are expandable and the step of positioning includes expanding the first and second tubular members against the vessel walls.

* * * * *